United States Patent
Madison

(10) Patent No.: US 7,655,023 B2
(45) Date of Patent: Feb. 2, 2010

(54) BLOOD VESSEL LOCATING AND STABILIZING DEVICE AND METHOD OF USING THE SAME

(75) Inventor: Michael T. Madison, Edina, MN (US)

(73) Assignee: Michael Madison, Edina, MN (US)

( * ) Notice: Subject to any disclaimer, the term of this patent is extended or adjusted under 35 U.S.C. 154(b) by 325 days.

(21) Appl. No.: 10/940,481

(22) Filed: Sep. 14, 2004

(65) Prior Publication Data

US 2006/0058839 A1    Mar. 16, 2006

(51) Int. Cl.
*A61B 17/00* (2006.01)

(52) U.S. Cl. ................................ 606/201; 604/115

(58) Field of Classification Search ......... 604/115–118, 604/179; 606/201–205, 213–217, 131; 128/888; D28/21, 44.2, 48, 52–54; 132/219, 323, 132/158, 159
See application file for complete search history.

(56) References Cited

U.S. PATENT DOCUMENTS

| | | | |
|---|---|---|---|
| 1,561,116 A | | 11/1925 | Silliman |
| 1,893,864 A | * | 1/1933 | Kocher .................... 132/157 |
| 2,103,174 A | | 12/1937 | Posada |
| 2,234,961 A | * | 3/1941 | Canada .................... 606/203 |
| 2,245,469 A | * | 6/1941 | Ecklund et al. ............. 7/163 |
| D150,039 S | * | 6/1948 | Utley ........................ D28/21 |
| 2,589,469 A | * | 3/1952 | Zerbo ........................ 132/219 |
| 3,292,641 A | * | 12/1966 | Quintanar .................. 132/210 |
| 3,324,854 A | | 6/1967 | Weese |
| 4,332,248 A | | 6/1982 | DeVitis |
| 4,513,842 A | * | 4/1985 | Karlsberg ................... 132/149 |
| 4,517,998 A | * | 5/1985 | Furco ........................ 132/148 |
| 4,572,182 A | | 2/1986 | Royse |
| 4,586,924 A | | 5/1986 | Lanning |
| 5,147,307 A | * | 9/1992 | Gluck ........................ 604/116 |
| 5,254,095 A | * | 10/1993 | Harvey ...................... 604/115 |
| 5,292,325 A | | 3/1994 | Gurmarnik |
| 5,415,647 A | * | 5/1995 | Pisarik ....................... 604/115 |
| 5,460,612 A | | 10/1995 | Madore |
| 5,728,178 A | | 3/1998 | Buffington et al. |
| 5,911,707 A | * | 6/1999 | Wolvek et al. ............. 604/116 |
| 6,652,487 B1 | * | 11/2003 | Cook ........................ 604/115 |

* cited by examiner

*Primary Examiner*—Anhtuan T Nguyen
*Assistant Examiner*—Kathleen Sonnett
(74) *Attorney, Agent, or Firm*—Stoel Rives LLP

(57) ABSTRACT

A blood vessel locating and stabilizing device including a transparent planar device that may be used to locate and stabilize a blood vessel so that the blood vessel is less likely to roll when it is punctured with a needle. The device is planar and includes a transparent region and a recess formed in a distal side surface that is configured to locate and stabilize a blood vessel. In a method of using the present device, the planar member is gripped along a first and second major surfaces of the device, the recess is positioned over the targeted blood vessel, and a force is applied to the device so that the blood vessel is located and stabilized.

19 Claims, 7 Drawing Sheets ns into a blood vessel, such as for example the femoral

BLOOD VESSEL LOCATING AND STABILIZING DEVICE AND METHOD OF USING THE SAME

FIELD OF THE INVENTION

The present invention is directed to a device for locating and stabilizing a blood vessel for puncture, and methods of using the device.

BACKGROUND OF THE INVENTION

Numerous medical procedures involve percutaneous insertions into a blood vessel, such as for example the femoral artery. Among the more common procedures are diagnostic and therapeutic intervention, such as for example balloon angioplasty and stent placement, brain artery catheterization, cardiac catheterization, intra-aortic balloon pumping (IABP) and percutaneous transluminal coronary angioplasty (PTCA). Each of these procedures typically begins with the placement of an angiographic needle through the skin and tissue of the patient's leg at a pulse point of the femoral artery immediately below the inguinal or groin crease. The needle is introduced until the tip of the needle has entered the femoral artery. A guidewire is then inserted through the needle and up through the femoral and iliac arteries until the guidewire reaches the desired location. The needle may then be removed, leaving the guidewire in place to serve as a guide for the insertion of an introducer sheath assembly.

It takes a considerable amount of skill to be able to locate a femoral artery or other targeted blood vessel, stabilize it, and then insert the needle so as to minimize pain to the patient. If the needle is not perfectly pointed towards the blood vessel, the blood vessel will often move laterally, or "roll," away from the needle as soon as the initial pressure is applied to the blood vessel. When the blood vessel rolls away from the needle or the needle misses the blood vessel, it is necessary to repeat the procedure causing discomfort and anxiety for the patient. Rolling is a particularly common problem because the blood vessel is embedded in soft tissue and has more mobility.

Traditionally, caregivers attempt to localize the path of the blood vessel with their fingers. This procedure however is fraught with the danger of the caregiver puncturing one of his or her fingers with the needle and being subjected to the risks of acquiring blood borne diseases such as hepatitis B and HIV infections and bacterial infections at the puncture site.

Various devices have been devised for vascular stabilization or positioning, such devices tend to be rather elaborate, requiring in many instances a positive mounting to the arm or the like. Known devices also tend to have limited utility insofar as being capable of accommodating, with a single instrument, the many variations that exist among different patients as well as the particular arteries and veins that are positioned, stabilized and retained during puncture.

One group of such devices at least partially blocks the flow of blood through the targeted blood vessel while stabilizing the vessel. Examples of such devices are described in U.S. Pat. No. 1,561,116 (Silliman), U.S. Pat. No. 3,324,854 (Weese), and U.S. Pat. No. 4,586,924 (Lanning). These devices generally include a surface portion that compresses the skin so that blood flow is restricted in the vessel. When force is applied to the portion against the skin, the vessel tends to bulge from the excess blood obstructed by the device. In particular, U.S. Pat. No. 1,561,116 (Silliman) describes a vein stabilizer that includes a handle and a substantially flat blade portion having a notch. The flat blade portion is adapted to be pressed over a distended vein to close one end of the vein so that the vein projects through the notch.

U.S. Pat. No. 2,103,174 (Posada) describes a device that restricts blood flow in a blood vessel with a strap and retains the blood vessel with a vein retaining plate. The strap serves as a tourniquet functioning to turn off or restrict the blood flow from the upper arm to the forearm. The vein retaining plate is made of spring metal material. The vein retaining plate is a substantially rectangular configuration and is dished or bowed so that the outer marginal edges of a pair or legs or arms lie in a plane above the plane of the inner marginal edges of said legs. The vein retaining plate also includes a convex strip that functions as a spring so that in the operation of the device, the width of the opening that extends between the inner edges of the arms or legs may be readily diminished by merely pressing the fingers on the sides of the arms or legs.

Another group of devices may allow blood to flow through the targeted blood vessel while it is stabilized, but do not allow for rotational positioning against the patient during stabilization to expose the targeted blood vessel. These types of devices are described in U.S. Pat. No. 4,332,248 (DeVitis), U.S. Pat. No. 5,254,095 (Harvey), and U.S. Pat. No. 5,415,647 (Pisarik). In particular, U.S. Pat. No. 5,254,095 (Harvey) describes a stabilizer for blood vessels that includes a pair of diverging panels integrally joined at a bight portion which in turn defines a hinge between the panels. The panels have outer edges with extending legs for engagement with and manipulation of the skin for the positioning and stabilizing of veins.

Still another group of devices do not stabilize a targeted blood vessel. Rather, these devices guide a needle into a blood vessel at a particular angle. U.S. Pat. No. 5,292,325 (Gurmarnik) describes a device and a method for facilitating subcutaneous introduction of a plastic carrier that includes an element having a supporting portion arranged to be supported on the skin of a patient, and a guiding portion extending substantially transversely to the supporting portion and having at least one slot formed so that when the supporting portion is placed on the skin of a patient and oriented on a surface projection line of an artery and a catheter is introduced through the slot of the guiding portion, the catheter is guided on an edge formed in the guiding portion by the slot so that a tip of the catheter is introduced exactly into the artery.

U.S. Pat. No. 5,911,707 (Wolvek, et al.) describes a needle guide that ensures that an angiographic needle is inserted into a patient's femoral artery at a prescribed location, angle and direction. The needle guide includes an elongated base having a recess on one end defined by a pair of projecting fingers, and a support member on the upper surface of the base adjacent to the recess. The support member has a support surface which is inclined at a prescribed angle with respect to a locating plane defined by the base. A channel in the support surface cradles and guides the angiographic needle at the prescribed angle as it is inserted into the femoral artery.

U.S. Pat. No. 4,572,182 (Royse) describes a pressure pad for use on an artery clamp of the type used to apply pressure following catheterization of a major artery. The pad includes a notched portion to facilitate placement of the pad over a catheter prior to removal of a catheter from a patient's artery. The pad is removably attached to an artery clamp.

BRIEF SUMMARY OF THE INVENTION

The present invention is directed to a device that is easily manually manipulated by one hand to provide an effective mechanism for locating and stabilizing a blood vessel, and particularly a femoral artery, for puncture. Such preparation, depending upon the nature and location of the blood vessel, will involve any or all of a series of actions utilizing the device in any of several orientations. One function of the device is to locate and stabilize or hold a blood vessel, particularly a femoral artery, in place. The device permits the physician's fingers to be off-set from the puncture site, increasing the safety of the physician. The present invention assists the user in moving excess abdominal skin and tissue from the inguinal or groin crease so as to expose the area of skin that covers the femoral artery. The present invention is particularly useful for inserting catheters.

The device includes a planar member and at least one recess that locates and stabilizes a blood vessel so that the blood vessel is less likely to shift or roll when punctured with a needle. The device may include more than one recesses to stabilize more than one blood vessel. For example, a device with two recesses may be used to isolate the femoral artery in one recess and isolate the femoral vein in another recess.

The device is preferably manufactured of a transparent material so that the user can see through the device and more carefully observe the needle as it is placed into the targeted blood vessel. The device is inexpensive to produce primarily because of readily available material and simple production. It is preferably disposable, thus avoiding the necessity for re-sterilization as required by the more complex and expensive devices that are intended for reuse.

In one embodiment, the blood vessel locating and stabilizing device includes a generally planar member that includes first and second major surfaces, first and second side surfaces, a proximal side surface and a distal side surface, a transparent region extending through at least the first and second major surfaces, and at least one recess formed in the distal side surface between the first and second side surfaces and extending through the first and second major surfaces, the recess having a configuration adapted to stabilize a blood vessel. The transparent region can also be an opening in a center region of the first and second planar surfaces.

The distal side surface preferably includes a rotation axis. The distal side surface is typically formed in a linear shape generally parallel to the rotation axis. In another embodiment, the distal side surface is formed in a curvilinear shape perpendicular to the rotation axis. The rounded edges of the device facilitate ease and comfort of movement against the skin, particularly when the device is used to move excess abdominal skin and tissue away from the inguinal crease.

The width between the side surfaces is preferably at least two times the thickness of the planar member measured between the first and second major surfaces. In another embodiment, the width between the side surfaces is at least three times or four times the thickness of the planar member. The thickness of the planar member measured between the first and second major surfaces is typically about 0.175 inches to about 0.325 inches, and more preferably about 0.25 inches.

In one embodiment, the transparent region is a transparent window substantially surrounded by an opaque region. The transparent region can be constructed from a first material substantially surrounded by an opaque region constructed from a second material. The transparent region can be plastic, glass, or a wide variety of transparent materials.

The side edges are preferably generally parallel. In another embodiment, the proximal side surface and distal side surface are generally parallel, while the side surfaces are not parallel. The present invention preferably includes an alignment feature accentuating the recess.

The recess can be configured in the shape of a semicircle, a polygon, a rectangle, a square, a triangle, an oval, a curvilinear shape, or a variety of other shapes. The recess is configured to apply a stabilizing force to a blood vessel along a longitudinal axis extending from the proximal side surface to the distal side surface, preferably without substantially restricting blood flow. The recess is preferably configured to apply a stabilizing force to the blood vessel without substantially restricting blood flow.

The recess is preferably oriented generally perpendicular to the first and second major surfaces. The recess can optionally be oriented at an angle relative to the first and second major surfaces. The present invention can optionally include a plurality of recesses.

The size of the recess relative to the blood vessel is important for some applications. For example, the femoral artery near the inguinal crease has a diameter of about 0.118 inches to about 0.236 inches (about 3 to about 6 millimeters). The cross-sectional area of the femoral artery in this region is about 0.011 square inches to about 0.044 square inches. In one femoral artery embodiment, the recess preferably has a cross-sectional area of about 0.019 square inches to about 0.066 square inches. Generally, the recess preferably has a cross-sectional area, measured in a plane parallel to the major surfaces, of between about ½ and about 6 times, and more preferably about 1 to about 3 times, the cross-sectional area of the blood vessel.

In another embodiment, the maximum height and maximum width of the recess is preferably about 3 times, and more preferably about 2 times the diameter of the blood vessel. Where the blood vessel is the femoral artery, the recess includes a width measure parallel to the distal side surface preferably of about 0.219 inches to about 0.406 inches, and more preferably about 0.3125 inches. The recess includes a height measured perpendicular to the distal side surface preferably about 0.175 inches to about 0.325 inches, and more preferably about 0.25 inches.

The present invention is also directed to a method of locating and stabilizing blood vessels. The method includes the steps of gripping a generally planar member along first and second major surfaces. The recess formed in a distal side surface of the planar member is positioned generally over the blood vessel. A first force is applied to a proximal side surface of the planar member along a longitudinal axis extending generally from the proximal side surface to the distal side surfaces. The first force delivers a stabilize force to the blood vessel.

The present method includes delivering the stabilizing force perpendicular to a rotation axis located in the distal side surface of the planar member. The planar member is optionally rotated around the rotation axis. Rotation of the planar member preferably occurs before the stabilizing force is applied to the blood vessel. The stabilizing force preferably permits a substantially free flow of blood in the blood vessel when the stabilizing force is applied. The present method includes viewing the skin through a transparent region and inserting a needle into the blood vessel using the recess and alignment line as a guide.

BRIEF DESCRIPTION OF THE SEVERAL VIEWS OF THE DRAWING

FIG. 1b illustrates a side view of the device of FIG. 1a.

FIG. 7b is a cross-sectional view of the device of FIG. 7a.

DETAILED DESCRIPTION OF THE INVENTION

Figure 1A:
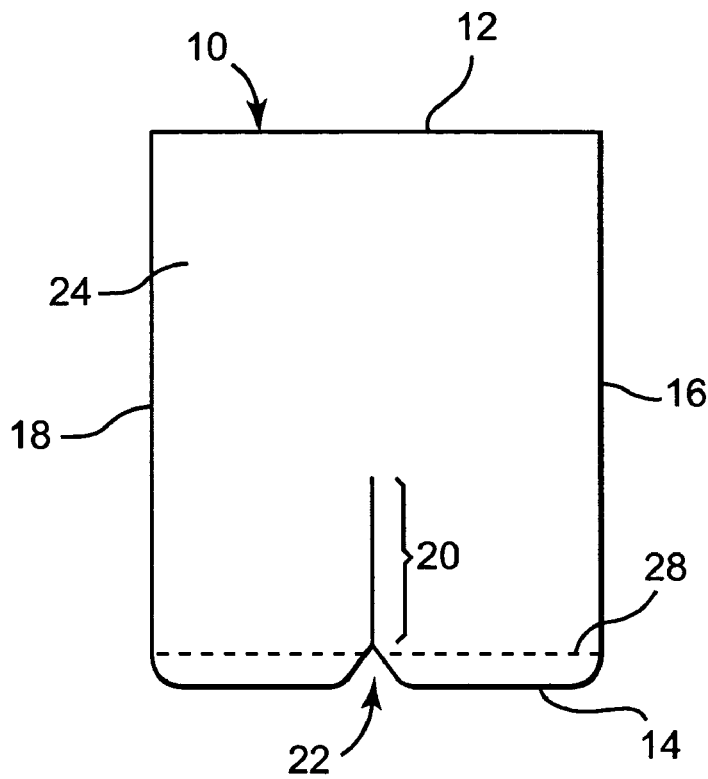
FIG. 1a is a front view of a blood vessel locating and stabilizing device in accordance with the present invention.

The present invention is directed to a blood vessel locating and stabilizing device that is formed of a planar member that includes a transparent region and at least one recess that is able to engage with and stabilize a blood vessel. As used herein, references to stabilizing a blood vessel and variations thereof, refer to constraining the movement of a blood vessel in at least two degrees of freedom. The present blood vessel locating and stabilizing device typically restricts the blood vessel's side-to-side movement and movement normal to the surface of the skin immediately above the blood vessel. The present blood vessel locating and stabilizing device also limits the skew of the blood vessel relative to the recess.

The length of the device permits the physician fingers to be off-set from the puncture site, reducing the risk of the physician puncturing his or her own fingers. This feature is particularly important when treating patients with contagious diseases, such as HIV or hepatitis.

The planar member is surrounded on the perimeter by proximal and distal side surfaces, and first and second side edges. The planar member also includes a first major surface and a second major surface that have greater surface areas than the surface areas of the proximal and distal side surfaces and the first and second side edges.

The dimensions of the planar member may be defined by its width and thickness. The width of the planar member is a distance between the first side surface and the second side surface. The thickness of the planar member is a distance between the first major surface and the second major surface. The thickness of the planar member may be any suitable thickness, such as, for example, about 0.5 inches or less, more particularly about 0.25 inches or less. In the preferred embodiment, the thickness of the planar member measured between the first and second major surfaces is typically about 0.175 inches to about 0.325 inches, and more preferably about 0.25 inches. The width of the planar member may be at least two times the thickness of the planar member, more particularly at least three times the thickness of the planar member, even more particularly at least four times the thickness of the planar member.

The transparent region of the planar member extends through the first and second major surfaces and allows a user to see through the device and more carefully observe a needle as it is placed into the targeted blood vessel. To this end, the planar member may be manufactured of any suitable transparent material such as clear plastic, glass, or any other monolithic transparent material. The transparent region can also be an opening in a center region of the first and second planar surfaces.

The recess is configured to locate and stabilize a blood vessel. The recess may function to isolate, hold, or otherwise segregate the blood vessel from the surrounding tissue. The recess extends through the first and second major surfaces and may be configured in any suitable shape such as a semicircle, a polygon, a rectangle, a square, a triangle, an oval, or a curvilinear shape. The recess may be formed perpendicular to the plane of the first and second major surfaces. Alternatively, the recess may be formed at an angle to the first and second major surfaces so that the recess is larger on one major surface and is smaller on the other major surface.

Figure 1B:
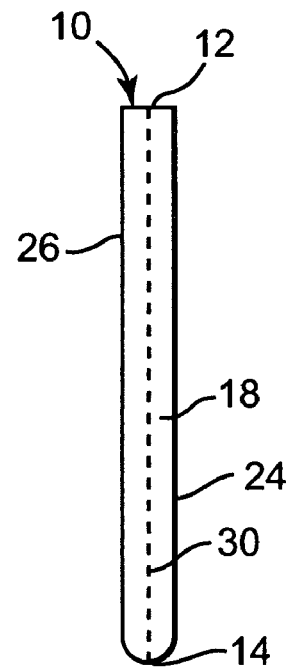

As illustrated in FIGS. 1a and 1b, device 10 includes a transparent planar member that includes a proximal side surface 12, a distal side surface 14, a first side surface 16, a second side surface 18, a first major surface 24 and a second major surface 26. Recess 22 is formed in the distal side surface 14 between the first side surface 16 and the second side surface 18. In the illustrated embodiment, the recess 22 is perpendicular to the first and second major surfaces 24, 26 and is configured in the shape of a triangle.

The size of the recess 22 is preferably selected as a function of the size of the blood vessel. For example, the femoral artery near the inguinal crease has a diameter of about 0.118 inches to about 0.236 inches (about 3 to about 6 millimeters). The cross-sectional area of the femoral artery in this region is about 0.011 square inches to about 0.044 square inches. The recess preferably has a cross-sectional area, measured in a plane parallel to the major surfaces, of between about ½ and about 6 times the cross-sectional area of the femoral artery. In one femoral artery embodiment, the recess preferably has a cross-sectional area of about 0.019 square inches to about 0.066 square inches. More generally, the recess preferably has a cross-sectional area of between about ½ and about 6 times, and more preferably about 1 to about 3 times the cross-sectional area of the blood vessel.

The maximum height and width of the recess is also relevant for some applications. The height and width of the recess 22 is preferably less than or equal to about 3 times, and more preferably about 2 times, the diameter of the blood vessel. In one femoral artery embodiment, the recess includes a width measure parallel to the distal side surface preferably of about 0.219 inches to about 0.406 inches, and more preferably about 0.3125 inches, and a height measured perpendicular to the distal side surface preferably about 0.175 inches to about 0.325 inches, and more preferably about 0.25 inches.

An alignment feature 20 is optionally included in this embodiment. The alignment feature may be any suitable mark that points to a recess and assists the user in placing a recess over a targeted blood vessel. In the embodiment of FIG. 1, the alignment feature 20 is a line that is etched or cut into the first major surface 24 of the planar member. However, the alignment feature 20 may be virtually any visible marking, of a wide variety of shapes and/or colors that accentuates the recess 22.

The distal side surface 14 preferably includes a rotation axis 28. The rotation axis 28 is the axis around which the planar member rotates when the distal side surface 14 is placed over the targeted blood vessel and the proximal side surface 12 is lifted to rotate the device 10 (see e.g., FIGS. 8a and 8b).

The distal side surface 14 in this embodiment is formed in a curvilinear shape perpendicular to the rotation axis 28. This feature can be seen in FIG. 1b. With the curvilinear shape, the distal side surface 14 is more easily rotated around the rotation axis 28, and the device 10 is more comfortable for the patient. The proximal side surface 12, first side surface 16 and second side surface 18 may also have curvilinear surfaces.

The device 10 also contains a longitudinal axis 30 that is perpendicular to the rotational axis 28 and runs between the proximal side surface 12 and the distal side surface 14. The longitudinal axis 30 is an axis along which a first force is delivered a stabilizing force to a blood vessel engaged with the recess 22.

Figure 2:
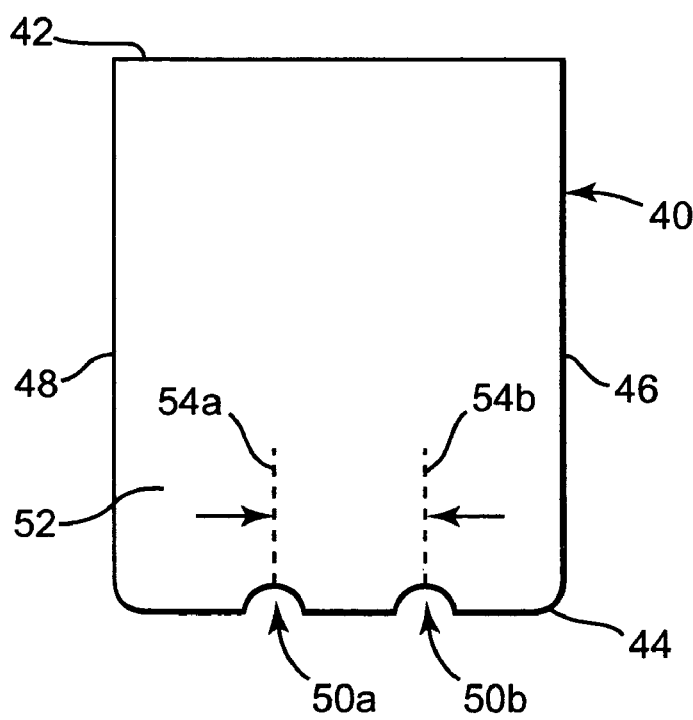
FIG. 2 is a front view of an alternate blood vessel locating and stabilizing device with a pair of semi-circular recesses in accordance with the present invention.

FIG. 2 illustrates another embodiment of a blood vessel locating and stabilizing device 40 with two semi-circular recesses 50a, 50b in accordance with the present invention. The planar member includes a proximal side surface 42, a distal side surface 44, a first side surface 46, a second side surface 48, a first major surface 52, and a second major surface, not shown. In this embodiment, the two recesses 50a, 50b are formed in the distal side surface 44 between the first side surface 46 and the second side surface 48. The spacing between the recesses 50a, 50b is preferably configured to stabilize adjacent blood vessels on the patient. For example, if the blood vessels are located near the inguinal crease, the separation between the center lines 54a, 54b of the recesses 50a, 50b is preferably less than about 0.197 inches, and more preferably less than about 0.079 inches to about 0.118 inches. For some applications, the adjacent recesses 50a, 50b are immediately adjacent with less than 0.040 inches separation.

Figure 3:
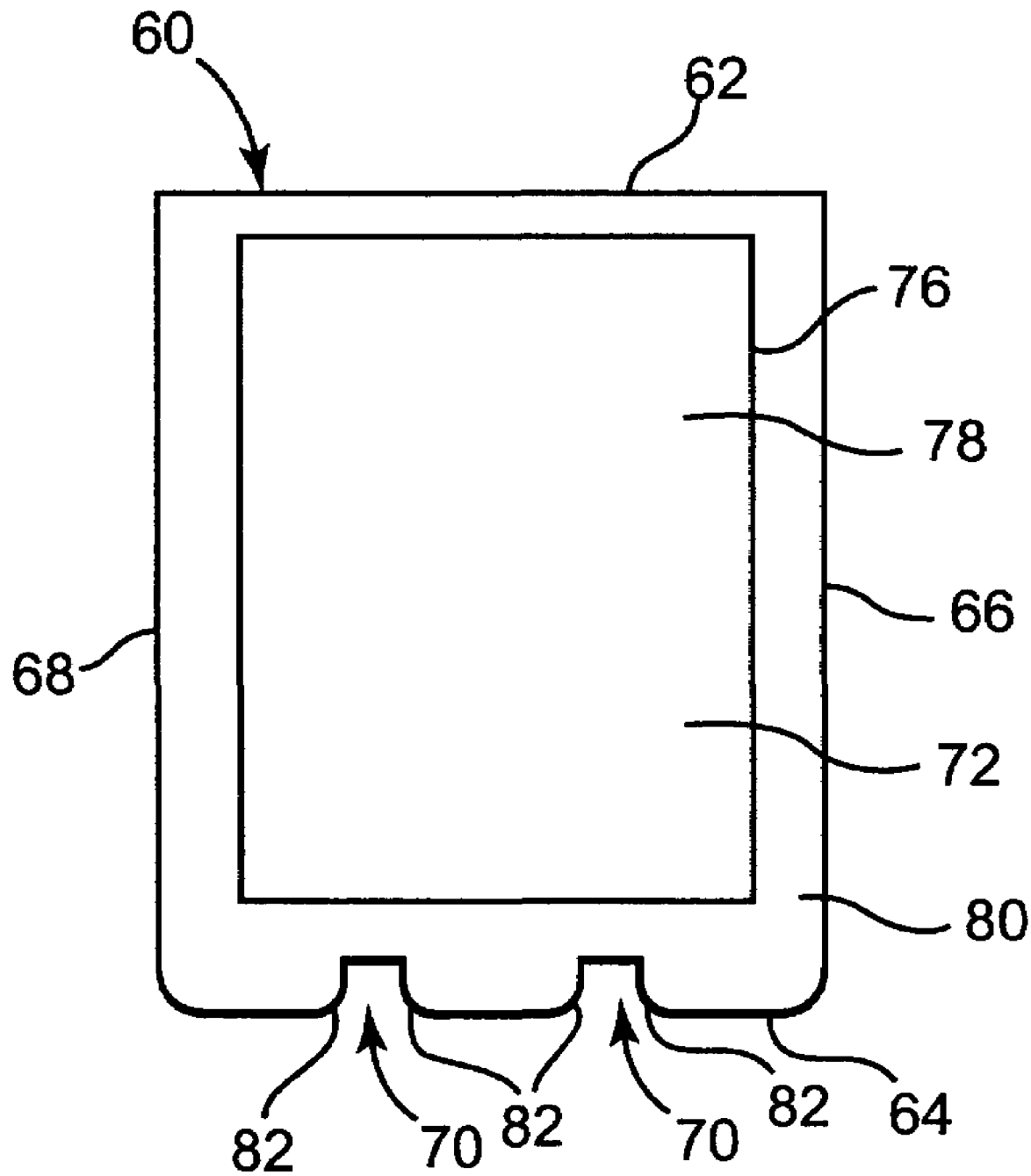
FIG. 3 is a front view of a blood vessel locating and stabilizing device with a transparent window surrounded by an opaque region in accordance with the present invention.

FIG. 3 illustrates still another embodiment in which a transparent region 78 of a device 60 is a transparent window 76 that is surrounded by an opaque or translucent region 80. The transparent window 76 extends through a first major surface 72 and a second major surface, not shown. The opaque region 80 is formed around the perimeter of the planar member and extends to a proximal side surface 62, a distal side surface 64, a first side surface 66, and a second side surface 68.

In this embodiment, the transparent window 76 may be constructed from a first material, while the opaque region 80 may be constructed from a second material. The transparent window 76 and the opaque region 80 may also include the same material. The two recesses 70 are each configured in the shape of a square. The location 82 where the recesses 70 meet the distal side surface 64 are preferably a curvilinear shape.

Figure 4:
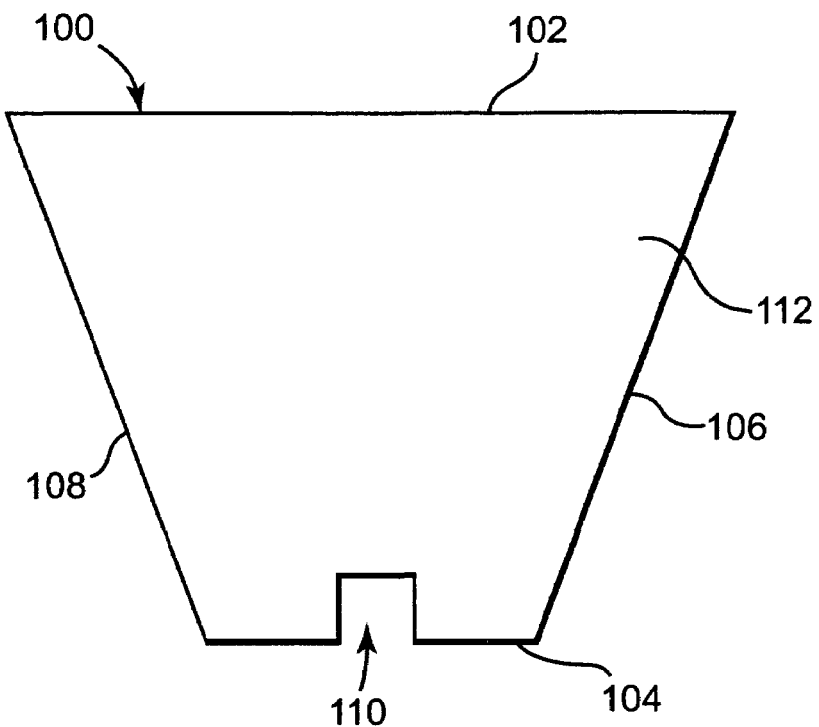
FIG. 4 is a front view of a blood vessel locating and stabilizing device with non-parallel side surface and a rectangular recess in accordance with the present invention.

FIG. 4 illustrates an alternate blood vessel locating and stabilizing device 100 formed in a trapezoidal shape. A first side surface 106 and a second side surface 108 are not parallel to each other while a proximal side surface 102 and a distal side surface 104 are generally parallel. The first major surface 112 is generally parallel to the second major surface, not shown. In this embodiment, the proximal side surface 102 is longer in distance than the distal side surface 104. A recess 110 is located in the distal side surface 104 and is configured in the shape of a square.

The shorter distal side surface 104 acts to increase the pressure around the blood vessel sought to be stabilized. By offering physicians several blood vessel locating and stabilizing devices 100 with distal side surfaces 104 of varying size, the optimum device can be selected for a given patient.

Figure 5:
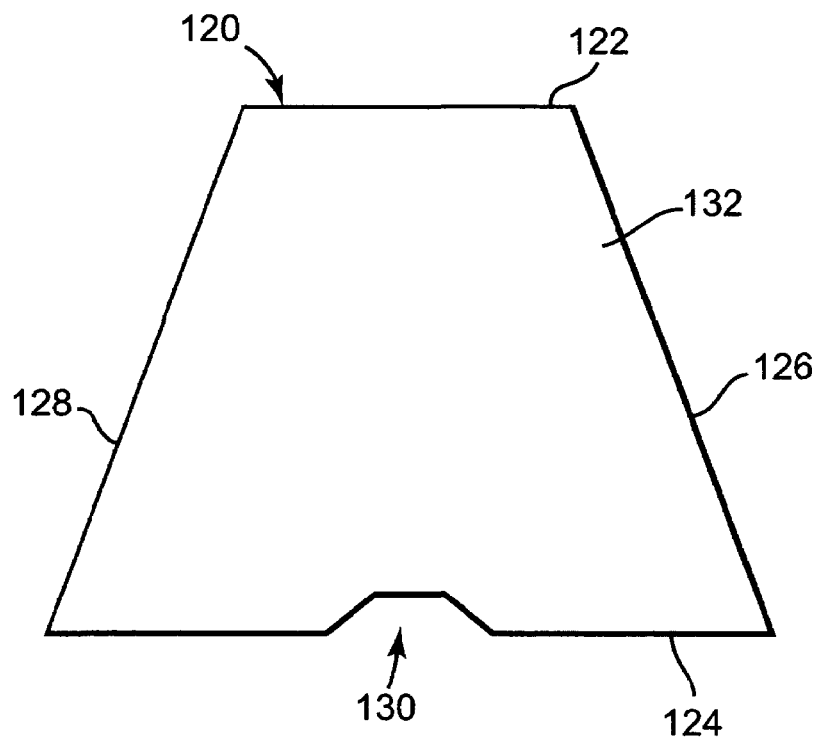
FIG. 5 is a front view of an alternate blood vessel locating and stabilizing device with non-parallel side surface and a polygonal recess in accordance with the present invention.

FIG. 5 illustrates another blood vessel locating and stabilizing device 120 formed in a trapezoidal shape. A first side surface 126 and a second side surface 128 are not parallel to each other while a proximal side surface 122 and a distal side surface 124 are parallel to each other. In this embodiment, the proximal side surface 122 is shorter in distance than the distal side surface 124. This embodiment also contains a recess 130 that is formed in the shape of a polygon. The longer distal side surface 124 has increased surface area, than for example the distal side surface 104 of FIG. 4, thereby reducing the pressure on the patient.

Figure 6:
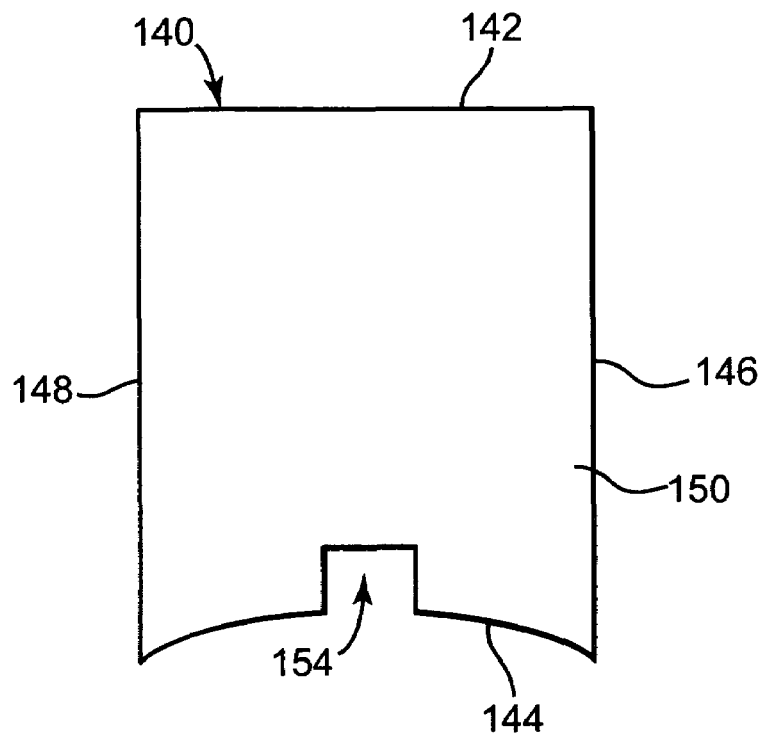
FIG. 6 is a front view of a blood vessel locating and stabilizing device in which distal side surface is concave in accordance with the present invention.

FIG. 6 illustrates a blood vessel locating and stabilizing device 140 that includes a curvilinear distal side surface 144 with a generally concave shape. Proximal side surface 142, a first side surface 146 and a second side surface 148 remain linear in this embodiment, although these side surfaces can be a variety of shapes in other embodiments. Recess 154 is configured in the shape of a square. The recess 154 is formed in the distal side surface 144 and is perpendicular to the first major surface 150. This embodiment may be particularly suitable if the targeted blood vessel is located in an area of the body that is convex or curved, such as, for example, the leg.

Figure 7A:
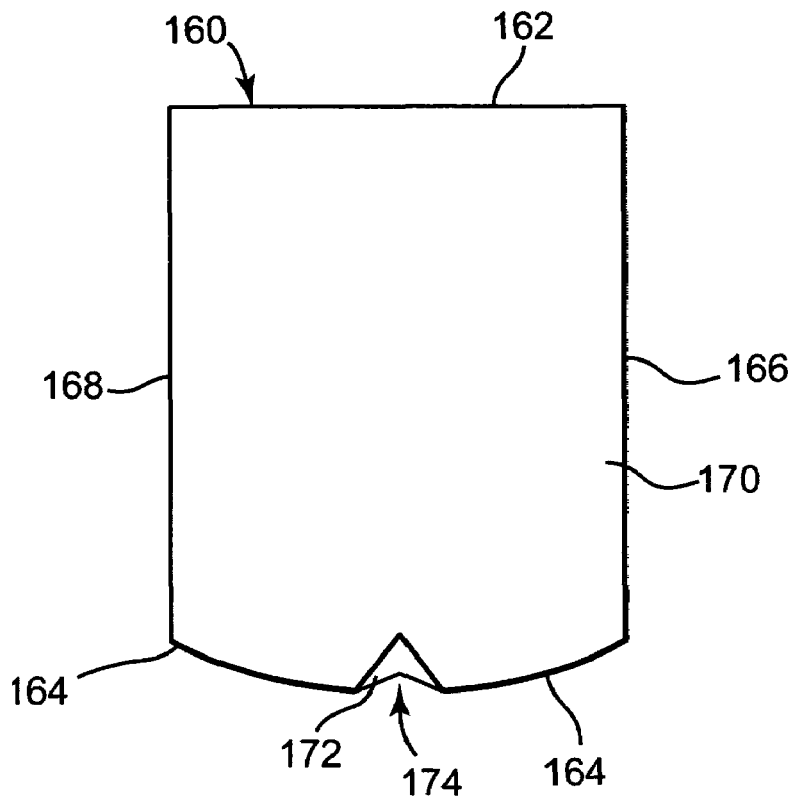
FIG. 7a is a front view of a blood vessel locating and stabilizing device in which a distal side surface is convex and the recess is formed at an angle to a first major surface and a second major surface in accordance with the present invention.
Figure 7B:
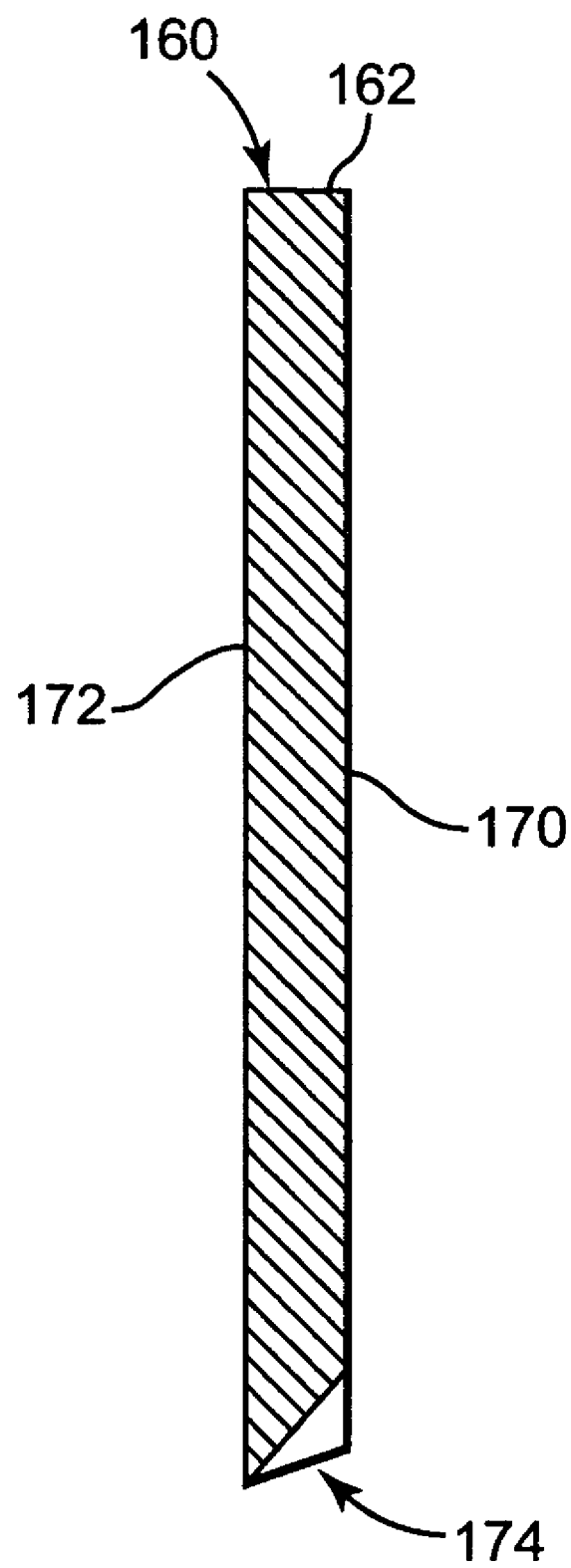

FIGS. 7a and b illustrate an embodiment of a blood vessel locating and stabilizing device 160 that includes a convex distal side surface 164, a linear proximal side surface 162, a linear first side surface 166, and a linear second side surface 168. In this embodiment, the distal side surface 164 is convex in shape. Recess 174 in this embodiment is a triangle shape that is formed at an angle relative to first major surface 170 and a second major surface 172. The recess 174 extends through the first major surface 170 and the second major surface 172, but is larger adjacent to the first major surface 170 and smaller adjacent to the second major surface 172.

Any of the various features of the embodiments discussed above can be combined in a wide variety of configurations of the present invention.

The present invention is also directed to a method of using the present blood vessel locating and stabilizing device. The planar member of the device is gripped. The recess formed in the distal side surface is positioned above the blood vessel. The user applies a force to the proximal side surface in the direction of the distal side surface along a longitudinal axis that is generally coplanar with the major surfaces of the device. This force delivers a stabilizing force to the blood vessel.

Figure 8A:
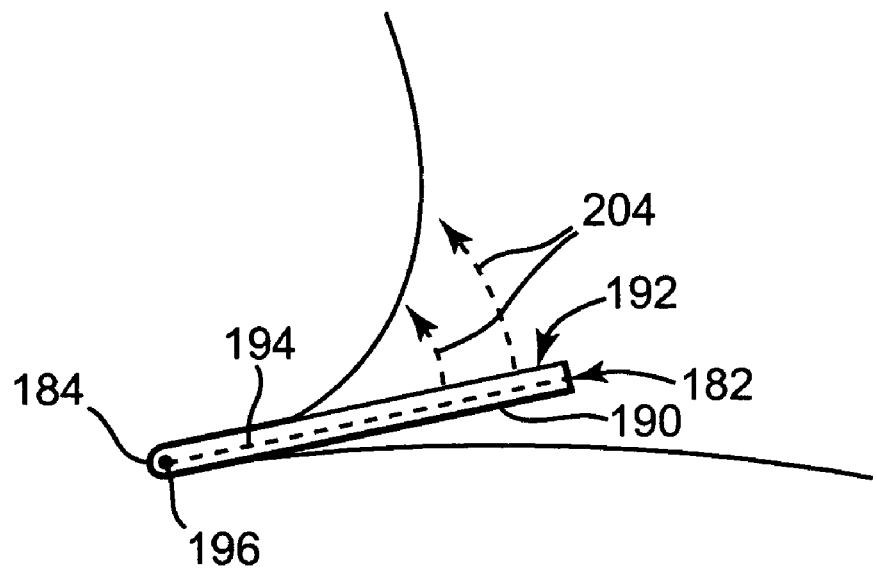
FIG. 8a illustrates one step of a method of using a blood vessel locating and stabilizing device of the present invention that includes positioning a distal side surface in the inguinal crease of a person and rotating the device around a rotation axis in accordance with the present invention.
Figure 8B:
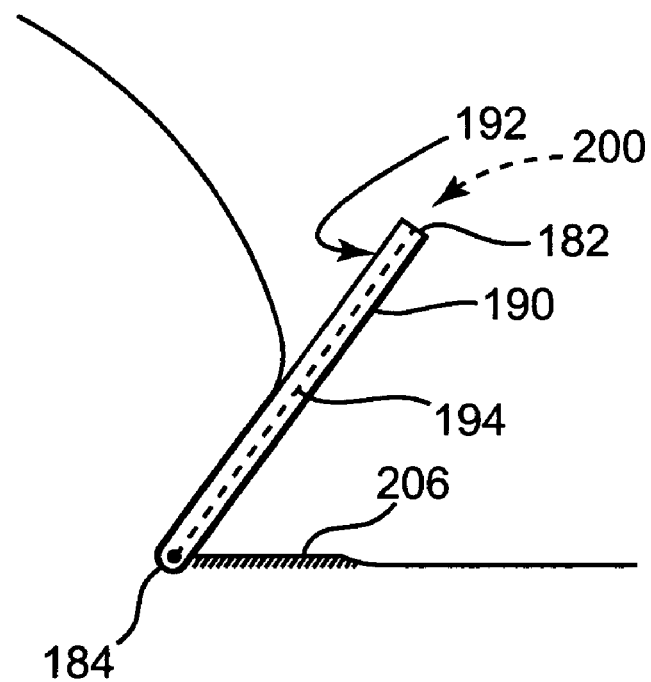
FIG. 8b illustrates another step of the method illustrated in FIG. 8a that includes applying a first force to a proximal side surface that travels along a longitudinal axis to a blood vessel engaged with a recess in accordance with the present invention.
Figure 8C:
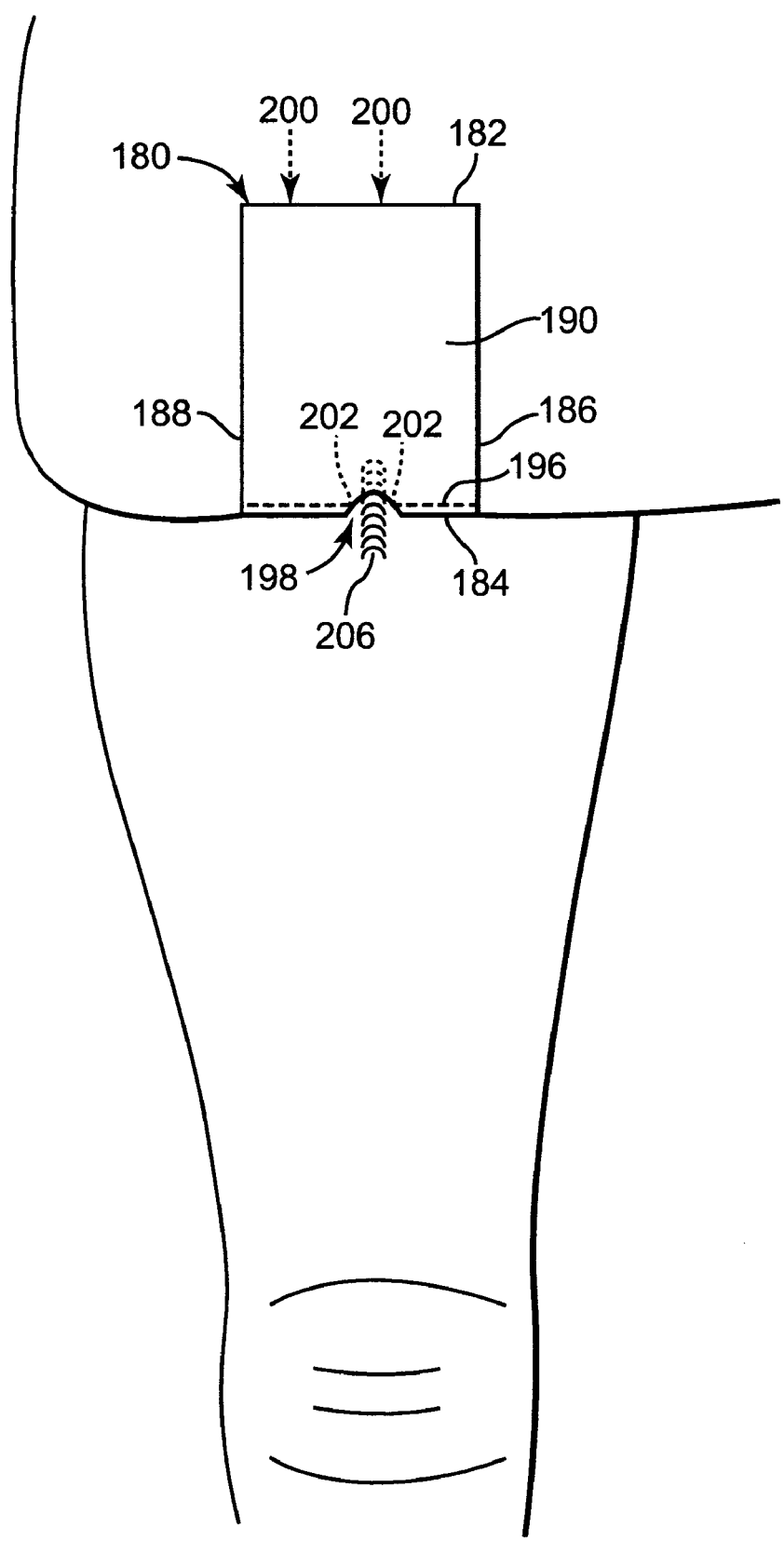
FIG. 8c illustrates a frontal view of the step illustrated in FIG. 8b.

In one embodiment of the method, illustrated in FIGS. 8a-c, a transparent device 180 is used to stabilize a femoral artery located in the inguinal crease. As illustrated in FIG. 8a, distal side surface 184 is placed in the inguinal crease where the femoral artery is located. Since excess abdominal skin and tissue can cover the inguinal crease in obese patients, the device 180 is slid into the crease to reach the femoral artery. A lifting force 204 is applied to a first major surface 190 of the planar member to lift the excess abdominal skin and tissue away from the femoral artery. The lifting force 204 causes the device 180 to rotate around a rotation axis 196 located in the distal side surface 184. The lifting force is sufficient to position the first major surface 190 and a second major surface 192 to a position of about 45 degrees with respect to the blood vessel 206.

As illustrated in FIG. 8b, a first force 200 is applied to proximal side surface 182 of the planar member. The first force 200 travels along a longitudinal axis 194, running from the proximal side surface 182 to the distal side surface 184, to deliver a stabilizing force 202 to the femoral artery 206 engaged in recess 198 in the distal side surface 184. In this method, the device 180 performs the function of stabilizing the femoral artery and pushing the excess skin and tissue away from the inguinal crease, making the blood vessel 206 more accessible. The second major surface 192 preferably provides sufficient surface area to keep the excess skin and tissue from blocking the targeted femoral artery 206.

FIG. 8c illustrates a frontal view of the step in which the first force 200 is applied to the proximal side surface 182 to deliver the stabilizing force 202 to the femoral artery 206 engaged with the recess 198. As illustrated, the first force 200 is sufficient to provide a stabilizing force 202 to the femoral artery, while also permitting a substantially free flow of blood through the femoral artery. Stabilized by the device, the user may then insert a needle into the femoral artery.

All patents and patent applications disclosed herein, including those disclosed in the Background of the Invention section, are hereby incorporated by reference. Although the present invention has been described with reference to preferred embodiments, workers skilled in the art will recognize that changes may be made in form and detail without departing from the spirit and scope of the invention. In addition, the invention is not to be taken as limited to all of the details thereof as modifications and variations thereof may be made without departing from the spirit or scope of the invention.

What is claimed is:

1. A device for locating and stabilizing a human blood vessel, the device comprising:
   a generally planar member comprising generally parallel first and second major surfaces, first and second side surfaces, a proximal side surface and a distal side surface, the distal side surface comprising a curvilinear shape perpendicular to a rotation axis, wherein the first and second major surfaces are adapted to be gripped by a user while the curvilinear shape is rotated into engagement with the blood vessel;
   a transparent region extending through at least a portion of the first and second major surfaces; and
   at least one recess formed in the distal side surface between the first and second side surfaces and extending into at least one of the first major surface and second major surfaces, the recess comprising a width measured parallel to the distal side surface of about 0.219 inches to about 0.406 inches, the distal side surface comprising a first substantially non-recessed segment extending from the first side surface to a first edge of the recess and a second substantially non-recessed segment extending from a second edge of the recess towards the second side surface, wherein a width of the first and second non-recessed segments is greater than a width of the recess measured generally parallel to the distal side surface.

2. The device of claim 1 wherein a width between the side surfaces comprises at least two times a thickness of the planar member measured between the first and second major surfaces.

3. The device of claim 1 wherein the transparent region comprises an opening in a center region of the first and second major surfaces.

4. The device of claim 1 wherein the transparent region comprises a transparent window substantially surrounded by an opaque region.

5. The device of claim 1 wherein the transparent region comprises one of clear plastic, glass, or a monolithic transparent material.

6. The device of claim 1 wherein the planar member comprises one of clear plastic, glass, or a monolithic transparent material.

7. The device of claim 1 comprising an alignment feature including a visible marking on the first major surface that points to and accentuates the recess.

8. The device of claim 1 wherein the recess comprises one of a semicircle, a polygon, a rectangle, a square, a triangle, an oval, or a curvilinear shape.

9. The device of claim 1 wherein the recess is oriented generally perpendicular to at least one of the first and second major surfaces.

10. The device of claim 1 wherein the recess is oriented at a non-perpendicular angle relative to at least one of the first and second major surfaces.

11. The device of claim 1 wherein the device comprises a plurality of recesses disposed between a plurality of substantially non-recessed segments.

12. The device of claim 1 wherein the distal side surface comprises a linear shape generally parallel to the rotation axis.

13. The device of claim 1 wherein the recess is configured to apply a stabilizing force to a blood vessel along a longitudinal axis extending from the proximal side surface to the distal side surface without substantially restricting blood flow.

14. The device of claim 1 wherein the recess comprises a height measured perpendicular to the distal side surface of about 0.175 inches to about 0.325 inches.

15. The device of claim 1 wherein the distal side surface is one of concave, convex, or curvilinear in a plane parallel to the first and second major surfaces.

16. A device for locating and stabilizing a human femoral artery, the device comprising:
    a generally planar member comprising generally parallel first and second major surfaces, first and second side surfaces, a proximal side surface and a distal side surface, wherein the distal side surface comprises a rotation axis and a curvilinear shape perpendicular to the rotation axis, wherein the first and second major surfaces are adapted to be gripped by a user while the curvilinear shape is rotated into engagement with a blood vessel; and
    at least one recess formed in the distal side surface between the first and second side surfaces and extending into at least one of the first major surface and second major surface, the recess comprising a width measured parallel to the distal side surface of about 0.219 inches to about 0.406 inches, the distal side surface further comprising a first substantially non-recessed segment extending from the first side surface to a first edge of the recess and a second substantially non-recessed segment extending from a second edge of the recess towards the second side surface, wherein a width of the first and second non-recessed segments is greater than a width of the recess measured generally parallel to the distal side surface.

17. The device of claim 16 wherein the recess comprises a non-perpendicular angle with respect to the first and second major surfaces.

18. A device for locating and stabilizing a human blood vessel, the device comprising:
    a generally planar member comprising generally parallel first and second major surfaces, first and second side surfaces, a proximal side surface and a distal side surface, wherein the distal side surface comprising a curvilinear shape perpendicular to a rotation axis, wherein the first and second major surfaces are adapted to be gripped by a user while the curvilinear shape is rotated into engagement with a blood vessel; and a single recess having a configuration adapted to stabilize the human blood vessel formed in the distal side surface between the first and second side surfaces, the recess comprising a first surface area in a plane of the first major surface and a second surface in a plane of the second major surface, wherein the second surface area is greater than the first surface area, the distal side surface further comprising a first substantially non-recessed segment extending from the first side surface to a first edge of the recess and a second substantially non-recessed segment extending from a second edge of the recess to the second side surface.

19. The device of claim 17 comprising a transparent region extending through at least a portion of the first and second major surfaces.

* * * * *